(12) United States Patent
Tanaka et al.

(10) Patent No.: US 10,451,408 B2
(45) Date of Patent: Oct. 22, 2019

(54) METHOD AND DEVICE FOR INSPECTING ENGRAVINGS IN TIRE MOLD

(71) Applicant: The Yokohama Rubber Co., LTD., Minato-ku, Tokyo (JP)

(72) Inventors: Tatsunori Tanaka, Hiratsuka (JP); Hirotaro Tada, Hiratsuka (JP); Shonosuke Motomiya, Hiratsuka (JP)

(73) Assignee: The Yokohama Rubber Co., Ltd. (JP)

( * ) Notice: Subject to any disclaimer, the term of this patent is extended or adjusted under 35 U.S.C. 154(b) by 32 days.

(21) Appl. No.: 15/302,946

(22) PCT Filed: Mar. 31, 2015

(86) PCT No.: PCT/JP2015/060140
§ 371 (c)(1),
(2) Date: Oct. 7, 2016

(87) PCT Pub. No.: WO2015/156172
PCT Pub. Date: Oct. 15, 2015

(65) Prior Publication Data
US 2017/0030709 A1    Feb. 2, 2017

(30) Foreign Application Priority Data

Apr. 7, 2014   (JP) ................................ 2014-078609

(51) Int. Cl.
*G06K 9/00*   (2006.01)
*G01B 11/24*   (2006.01)
(Continued)

(52) U.S. Cl.
CPC ............. *G01B 11/24* (2013.01); *G01N 21/95* (2013.01); *G06T 7/001* (2013.01); *G06T 7/0008* (2013.01);
(Continued)

(58) Field of Classification Search
CPC ......... G06T 7/0002; G06T 7/001; G06T 7/10; G06T 7/13; G06T 7/30; G06T 7/50;
(Continued)

(56) References Cited

U.S. PATENT DOCUMENTS 6,805,540 B2 * 10/2004 Ishihara ............. B29D 30/0606
425/28.1
7,177,740 B1 * 2/2007 Guangjun ........... G01M 17/027
73/146

(Continued)

FOREIGN PATENT DOCUMENTS

| JP | 2005-246931 | 9/2005 |
|---|---|---|
| JP | 2005-331274 | 12/2005 |

(Continued)

OTHER PUBLICATIONS

International Search Report for International Application No. PCT/JP2015/060140 dated Jun. 23, 2015, 4 pages, Japan.

*Primary Examiner* — Eric Rush
(74) *Attorney, Agent, or Firm* — Thorpe North & Western (57) ABSTRACT

A method for inspecting engravings in a tire mold includes inputting in advance into a data processing device two-dimensional image master data of an engraving formed on a surface of a side plate in a plan view using basic data set as a reference, the image master data having a radial component and a radial position of the engraving corrected on the basis of a locus length in a radial direction of the surface of the side plate; generating two-dimensional image actual measurement data, the image actual measurement data having a radial component and a radial position of three-dimensional data acquired via actual measurement corrected on the basis of a radial locus length of a surface of a side plate on which actual measurement was performed; and determining whether or not an image shape and an image (Continued)

position of the image actual measurement data is within a tolerable range.

4 Claims, 7 Drawing Sheets

(51) Int. Cl.
*G01N 21/95* (2006.01)
*G06T 7/00* (2017.01)
*G06T 7/33* (2017.01)

(52) U.S. Cl.
CPC .......... *G06T 7/337* (2017.01); *G01N 2201/12* (2013.01); *G06T 2207/10028* (2013.01); *G06T 2207/30116* (2013.01)

(58) Field of Classification Search
CPC .. G06T 7/521; G06T 7/60; G06T 7/70; G06T 7/73–75; G06T 7/0004; G06T 7/0006; G06T 7/0008; G06T 7/33; G06T 7/337; G06T 7/344; G06T 2207/10028; G06T 2207/30116; G01M 17/013; G01M 17/02; G01M 17/024; G01M 17/027; B60C 13/00; B60C 13/001; B60C 19/00; G01B 11/24; G01B 11/2433; G01B 11/25; G01B 11/2518; G01B 11/2522; G01N 21/88; G01N 21/8803; G01N 21/8806; G01N 21/8851; G01N 21/8887; G01N 21/95; G01N 21/956; G01N 2201/12; G06K 9/00201; G06K 9/00208
USPC ....... 382/100, 106, 108, 141, 152, 154, 282, 382/286, 291, 294–296; 702/33, 35, 36, 702/40, 81–84; 356/2, 3, 3.01, 3.03, 3.1, 356/4.01, 237.1, 237.2, 237.3, 237.4, 356/237.5, 394, 601, 603, 606; 73/115.07, 146; 700/143
See application file for complete search history.

(56) References Cited

U.S. PATENT DOCUMENTS

| | | | | |
|---|---|---|---|---|
| 7,738,120 | B2* | 6/2010 | Braghiroli | B60C 25/0554 356/614 |
| 7,997,129 | B2* | 8/2011 | Sukegawa | G01M 17/027 73/146.5 |
| 9,310,278 | B2* | 4/2016 | Sukegawa | G01N 21/952 |
| 10,118,448 | B2* | 11/2018 | Mizutani | G06T 7/74 |
| 2005/0058333 | A1* | 3/2005 | Kaneko | G06T 7/521 382/141 |
| 2007/0185610 | A1* | 8/2007 | Salamanca | B22D 5/02 700/197 |
| 2007/0209431 | A1* | 9/2007 | Fujisawa | G06K 9/2054 73/146 |
| 2009/0226073 | A1 | 9/2009 | Honda et al. | |
| 2010/0026799 | A1* | 2/2010 | Fujisawa | G06T 7/001 382/173 |
| 2011/0019903 | A1* | 1/2011 | Joly | G06T 7/33 382/141 |
| 2011/0069323 | A1* | 3/2011 | Takahashi | G06T 7/0004 356/625 |
| 2013/0266189 | A1* | 10/2013 | Vinciguerra | G06K 9/6207 382/104 |
| 2016/0086320 | A1* | 3/2016 | Fujisawa | G06T 7/001 382/141 |

FOREIGN PATENT DOCUMENTS

| | | | |
|---|---|---|---|
| JP | 2007-011462 | | 1/2007 |
| JP | 2007-333457 | | 12/2007 |
| JP | 2007333457 A | * | 12/2007 |
| JP | 2011-509398 | | 3/2011 |
| WO | WO 2005/111540 | | 11/2005 |
| WO | WO 2007/000909 | | 1/2007 |
| WO | WO 2009/077539 | | 6/2009 |

* cited by examiner

METHOD AND DEVICE FOR INSPECTING ENGRAVINGS IN TIRE MOLD

TECHNICAL FIELD

The present technology relates to a method and a device for inspecting engravings in a tire mold; and particularly relates to a method and a device for inspecting engravings in a tire mold capable of determining the suitability of engravings formed on a surface of an annular side plate, which is a component of the tire mold, in a reduced time and with high precision.

BACKGROUND ART

Various information, such as tire size, brand name, and design, is marked on the side surface of pneumatic tires. To mark such information on the tire side surface, engravings corresponding to this information are engraved on a surface of an annular side plate, which is a component of a tire mold. Upon manufacture of the side plate, various inspections are carried out, including whether the engravings formed on the surface of the side plate match the preset information, whether the position of the engravings is suitable, and whether the engravings have deteriorated.

Such engravings are small being only a few millimeters in size. Thus, visual inspection of the suitability of the engravings requires a great amount of time and effort.

A method of inspection is known that determines the acceptability of a raised or depressed character string formed on a side surface of a manufactured pneumatic tire (see Japanese Unexamined Patent Application Publication No. 2005-246931A). In the method of inspection of this patent document, an image of the raised or depressed character string formed on the tire side surface is captured and an image pattern of the character string is generated. Thereafter, how much the generated image pattern is a match with a preset model pattern is calculated, and this result determines whether the character string is acceptable or not.

In such a method of inspection, a degree of match is obtained by comparing the three-dimensional data of the raised or depressed character string for inspection against a reference (model pattern) raised or depressed character string three-dimensional data. However, processing the data to obtain a degree of match requires much time, and a high performance data processing machine with high processing speeds is required.

SUMMARY

The present technology provides a method and a device for inspecting engravings in a tire mold capable of determining the suitability of engravings formed on a surface of an annular side plate, which is a component of the tire mold, in a reduced time and with high precision.

A method of the present technology for inspecting engravings in a tire mold capable of determining suitability of an engraving formed on a surface of an annular side plate, which is a component of the tire mold, comprises the steps of:

inputting into a data processing device two-dimensional image master data of an engraving formed on a surface of a side plate in a plan view pregenerated using basic data set as a reference, the image master data having a radial component and a radial position of the engraving corrected on the basis of a locus length in a radial direction of the surface of the side plate;

acquiring three-dimensional data of the engraving by actual measurement of the manufactured side plate;

generating two-dimensional image actual measurement data, the image actual measurement data having a radial component and a radial position of the three-dimensional data corrected on the basis of a radial locus length of a surface of the side plate on which actual measurement was performed; and determining whether or not an image shape and an image position of the image actual measurement data is within a tolerable range with respect to an image shape and an image position of the image master data via comparison processing of image contours of the image master data and the image actual measurement data by the data processing device.

A device of the present technology for inspecting engravings in a tire mold capable of determining suitability of an engraving formed on a surface of an annular side plate, which is a component of the tire mold, comprises:

a data processing device configured to receive two-dimensional image master data of an engraving formed on a surface of a side plate in a plan view using basic data set as a reference, the image master data having a radial component and a radial position of the engraving corrected on the basis of a locus length in a radial direction of the surface of the side plate; and a measuring unit configured to acquire three-dimensional data of the engraving by actual measurement of the manufactured side plate; wherein two-dimensional image actual measurement data is generated by the data processing device, the image actual measurement data having a radial component and a radial position of the three-dimensional data corrected on the basis of a radial locus length of a surface of the side plate on which actual measurement was performed; and whether or not an image shape and an image position of the image actual measurement data is within a tolerable range with respect to an image shape and an image position of the image master data is determined via comparison processing of image contours of the image master data and the image actual measurement data by the data processing device.

According to the present technology, the two-dimensional image master data of the engraving in a plan view is pregenerated using basic data set as a reference. In the image master data, the radial component and the radial position of the engraving formed on the surface are corrected on the basis of the locus length in the radial direction of the surface of the side plate. Comparison of the image contours of the image actual measurement data and the image master data is made possible by the generation of two-dimensional image actual measurement data. The two-dimensional image actual measurement data is generated by acquiring three-dimensional data of the engraving by the actual measurement of the manufactured side plate, and then correcting the radial component and the radial position of the three-dimensional data on the basis of the radial locus length of the surface of the side plate on which actual measurement was performed. By comparing the two-dimensional data by comparison processing, it can be determined whether or not the image shape and the image position of the image actual measurement data is within a tolerable range with respect to the image shape and the image position of the image master data in a reduced inspection time and with high precision. Accordingly, the inspection target engraving can be determined as suitable or not against the master data, which serves as a suitability determination reference.

DETAILED DESCRIPTION

Below, a method and a device for inspecting engravings in a tire mold of the present technology will be described referencing embodiments illustrated in the drawings.

Figure 1:
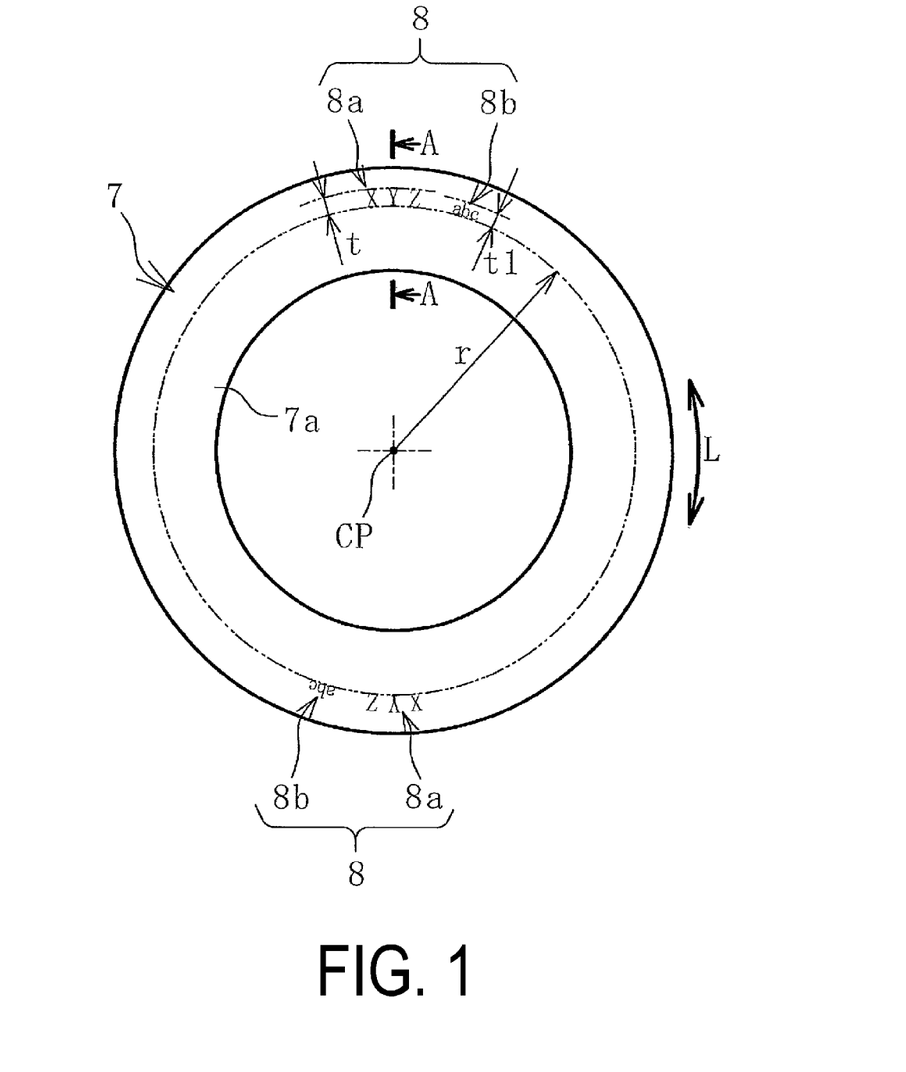
FIG. 1 is an explanatory view illustrating in a plan view a manufactured side plate.

The method and the device for inspecting engravings in a tire mold of the present technology are used to determine whether or not an engraving 8 (8a, 8b) is within a tolerable range with respect to a preset reference (image master data 9 described below) and suitable. The engraving 8 is formed on a surface 7a of an annular side plate 7 exemplified in FIG. 1, which is a component of the tire mold.

Various engravings 8a, 8b, such as tire size and brand name, are formed on the surface 7a of the manufactured side plate 7. The engraving 8 may be constituted by characters, numbers, designs, or the like and is raised or depressed with respect to the surface 7a. In a plan view, the innermost circumferential position of the engraving 8a is a position of radial distance r from an annular center point CP of the side plate 7. The engraving 8a has a size equivalent to radial length t. The innermost circumferential position of another engraving 8b is also a position of the radial distance r from the center point CP. The engraving 8b has a size equivalent to radial length t1 (t>t1). The position and the size of the engravings 8 are set separately. These engravings 8 may be disposed at a single position on the surface 7a of the side plate 7 or may be disposed at a plurality of positions at appropriate intervals in the circumferential direction L of the side plate 7.

Figure 2:
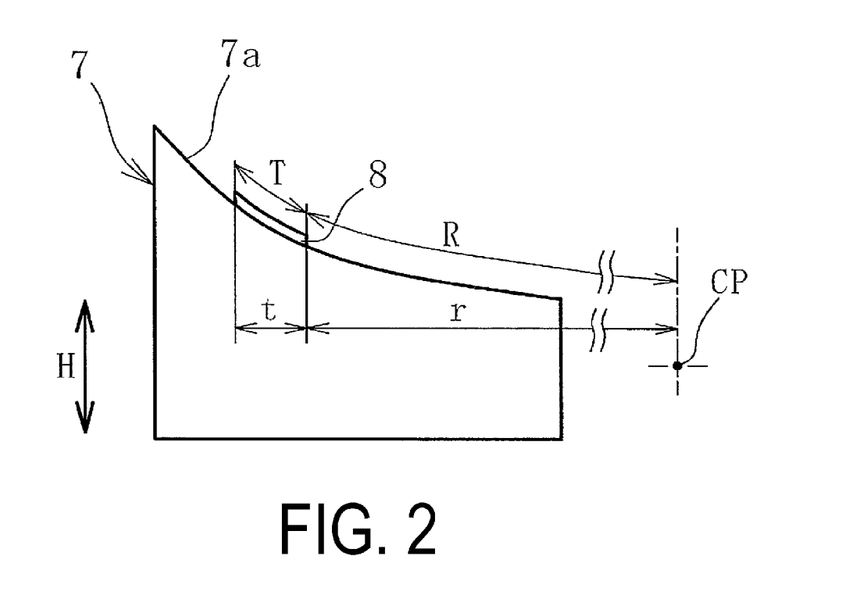
FIG. 2 is an explanatory view illustrating a cross section taken along A-A of FIG. 1.

Typically, the surface 7a of the side plate 7 is a curved surface with its dimensions in the thickness direction H varying in accordance with the radial distance, as exemplified in FIG. 2. Accordingly, the radial distance r in a plan view is equivalent to radial distance R, which is a distance along the curved surface of the surface 7a when viewed in the cross section of FIG. 2. In other words, when the radial distance r is corrected on the basis of the locus length in the radial direction of the surface 7a of the side plate 7, it becomes radial distance R. In a similar manner, when the radial length t of the engraving 8 in a plan view is corrected on the basis of the locus length in the radial direction of the surface 7a, it becomes radial length T.

Figure 3:
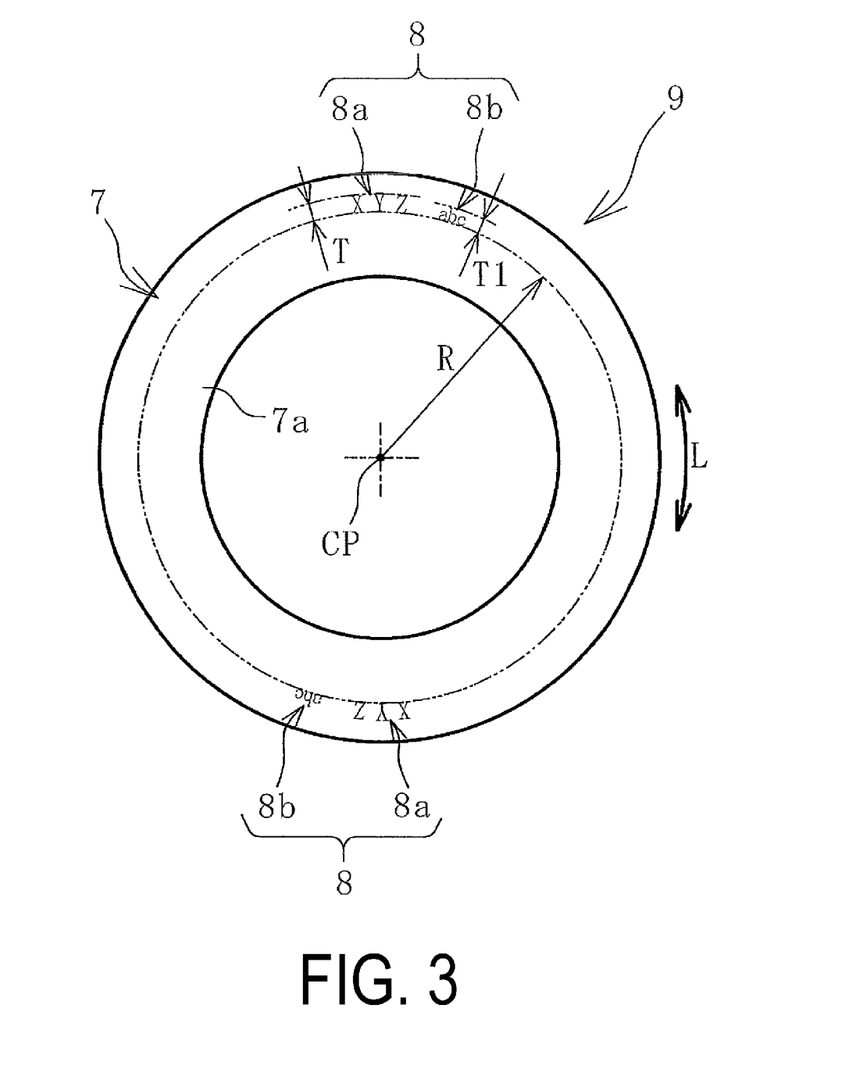
FIG. 3 is an explanatory view illustrating image master data.

In the present technology, a two-dimensional image master data 9 of the engravings 8 in a plan view, as exemplified in FIG. 3, is generated using basic data set as a reference. In the image master data 9, the radial component t, t1 (radial length t, t1) and the radial position r of the engraving 8 formed on the surface 7a are corrected on the basis of the locus length in the radial direction of the surface 7a of the side plate 7. In the image master data 9, the innermost circumferential position of the engravings 8 is the radial position R, and the engravings 8 have the radial length T, T1. Note that in the image master data 9, the basic data set as the reference can be design or manufacturing data of the side plate 7, data acquired from a completed, non-defective product, and the like.

Figure 4:
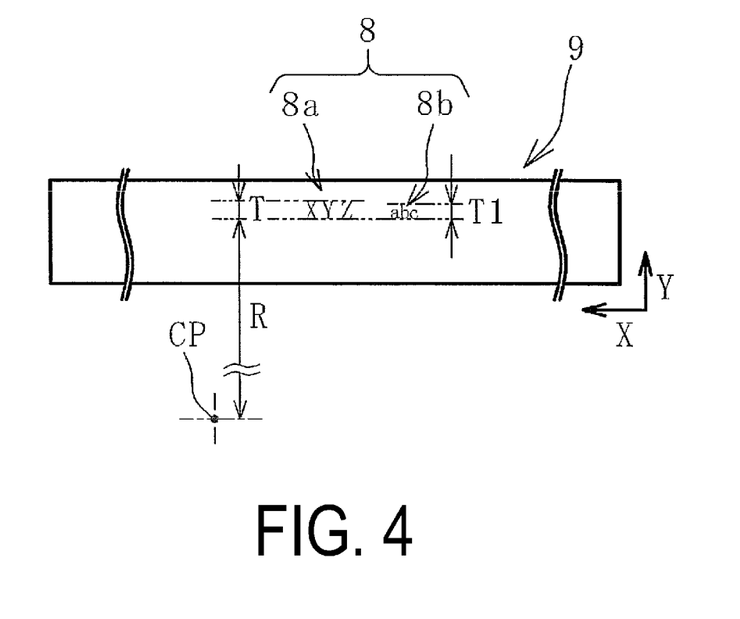
FIG. 4 is an explanatory view illustrating rectangularized image master data.

The two-dimensional image master data 9 is processed to rectangularize the data as illustrated in FIG. 4, for example. In FIG. 4, the X direction corresponds to the circumferential direction L of the side plate 7, and the Y direction corresponds to the radial direction of the side plate 7.

Figure 5:
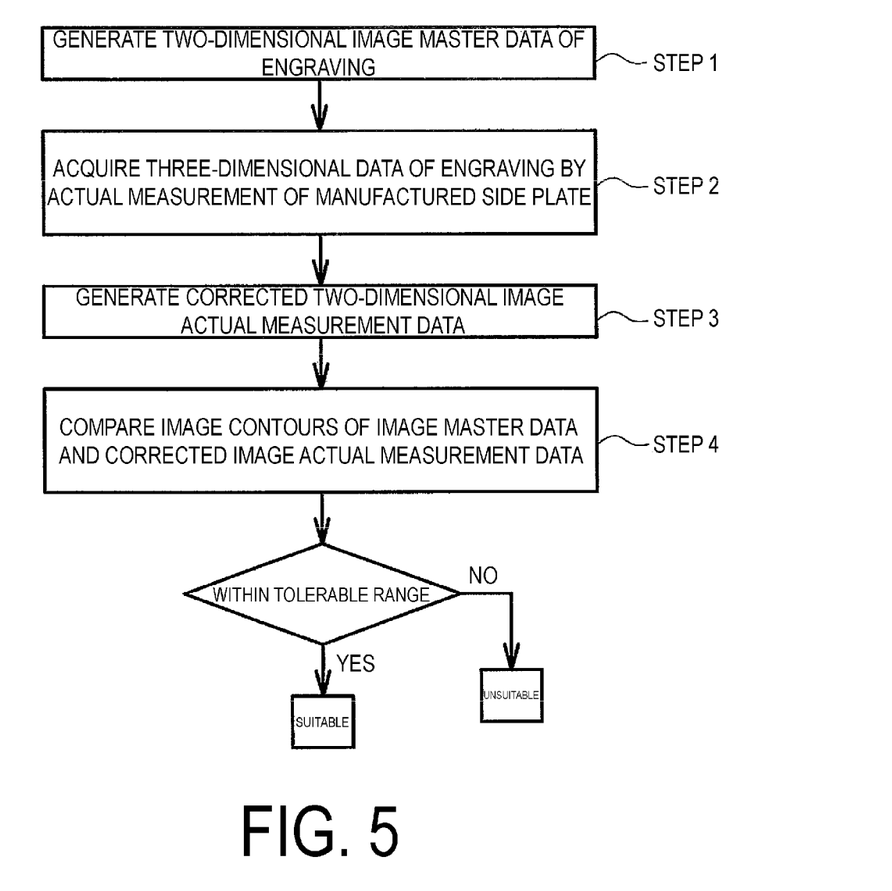
FIG. 5 is a flow chart of the steps of an inspection method of the present technology.

The method for inspection of the present technology is carried out on the basis of the flow chart exemplified in FIG. 5. First, as described above, the two-dimensional image master data 9 of the engravings 8 in a plan view is generated (step 1).

Next, actual measurements of the manufactured side plate 7 are taken, and the three-dimensional data of the engravings 8 is acquired (step 2). Upon actual measurement of the side plate 7, an inspection device 1 for engravings in the tire mold of the present technology (hereinafter referred to as "inspection device 1") as exemplified in FIG. 6 is used.

Figure 6:
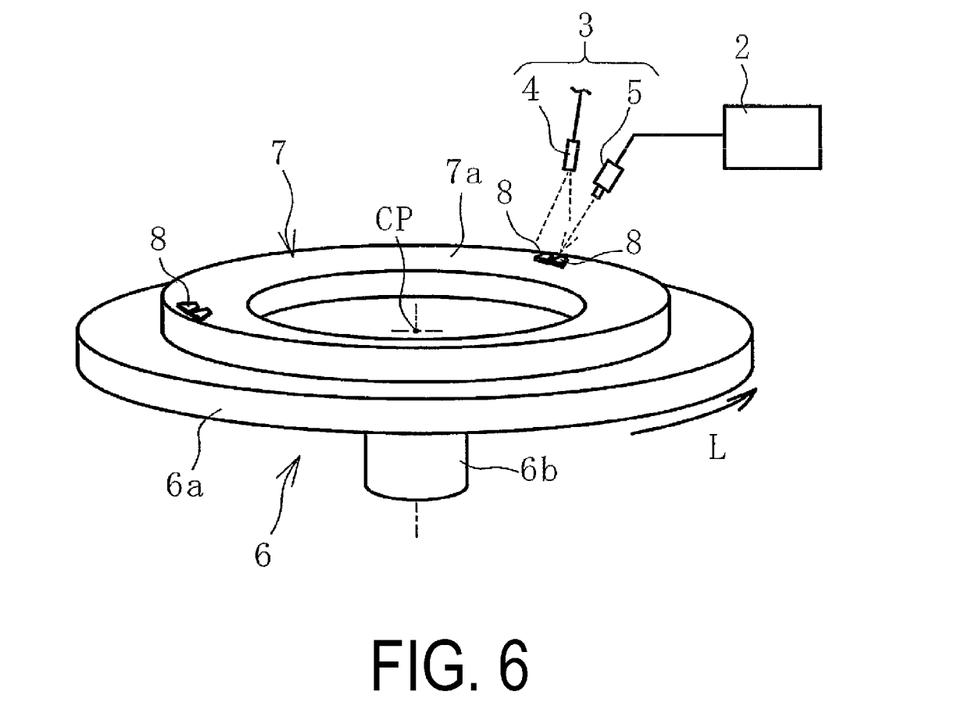
FIG. 6 is an explanatory view schematically illustrating an inspection device of the present technology.

The inspection device 1 exemplified in FIG. 6 includes a data processing device 2 such as a computer, and a measuring unit 3 configured to take actual measurements of the manufactured side plate 7 and acquire the three-dimensional data of the engravings 8 formed on the surface 7a of the side plate 7. The image master data 9 described above is input into the data processing device 2.

In this embodiment, the measuring unit 3 includes an irradiating device 4 configured to irradiate the surface 7a of the side plate 7 with a laser, and a camera device 5. The camera device 5 is configured to capture an image of the engravings 8 irradiated by the laser and acquire three-dimensional data of the engravings 8.

Additionally, the inspection device 1 includes a rotation mechanism 6 configured to actuate rotational movement of the side plate 7 and the camera device 5 relative to one another about the annular center point CP of the manufactured side plate 7. The rotation mechanism 6 is constituted by, for example, a rotational plate 6a on which the side plate 7 is placed and a drive unit 6b configured to drive in rotation the rotational plate 6a. In this embodiment, the camera device 5 is fixed at a certain position, and the side plate 7 together with the rotational plate 6a move in rotation about the annular center point CP. Images of the engravings 8 are captured while the side plate 7 is rotated in the circumferential direction L to acquire three-dimensional data of the engravings 8 for one revolution of the side plate 7. The side plate 7 can be fixed at a certain position and the camera device 5 moved in rotation about the annular center point CP.

The data processing device 2, for example, substitutes the radial components (radial length) and the thickness components of the acquired three-dimensional data of the engravings 8 for values and converts the data to a greyscale image. Here, the image master data 9 is corrected as described above, thus as is the case with the acquired three-dimensional data, the radial component (radial length) and the radial position of the surface 7a of the side plate 7 is corrected on the basis of the actual measurement of the radial locus length of the surface 7a of the side plate 7 to generate two-dimensional image actual measurement data 10 as exemplified in FIG. 7 (step 3).

Figure 7:
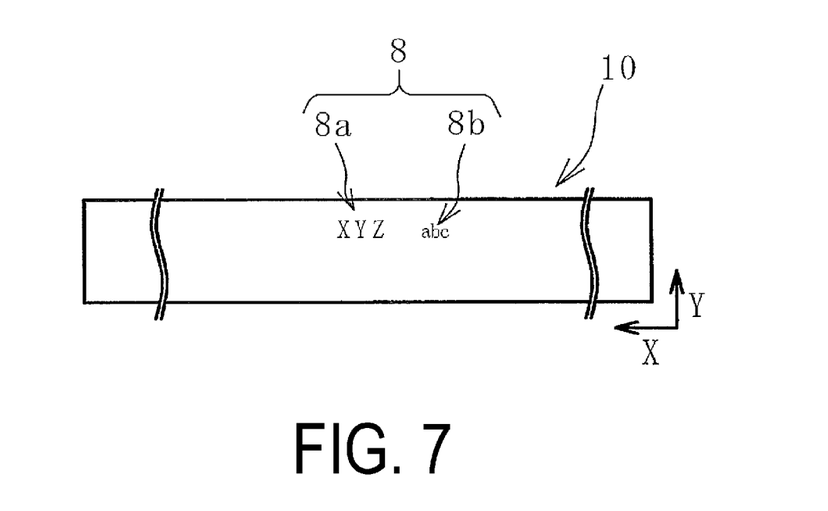
FIG. 7 is an explanatory view illustrating corrected image actual measurement data.

This correction allows for comparison of the image master data 9 and the image actual measurement data 10.

Figure 8:
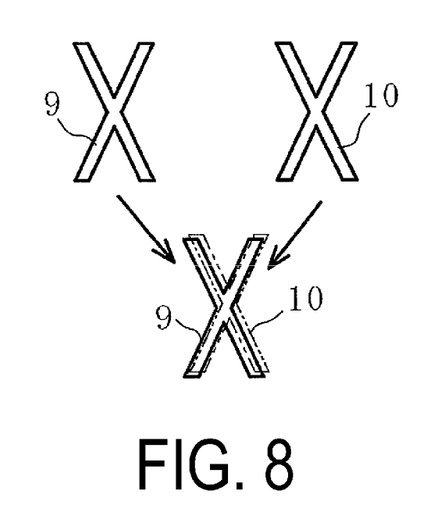
FIG. 8 is an explanatory view illustrating the step of comparison processing of image contours of the image master data of FIG. 4 and the image actual measurement data of FIG. 7.

Next, the data processing device 2 performs comparison processing on the image contours of the image master data 9 and the image actual measurement data 10 as exemplified in FIG. 8 (step 4). In the comparison processing, it is determined whether or not the image shape and the image position of the image actual measurement data 10 is within a tolerable range with respect to the image shape and the image position of the image master data 9. In other words, the image master data 9 (the letter "X" in FIG. 8) and the image actual measurement data 10 (the letter "X" in FIG. 8) are aligned so as to overlap. The tolerable range in terms of the degree of match of the image shape and the misalignment of the two is preset and input into the data processing device 2.

If the result of the comparison of the two is that the image shape and the image position of the image actual measurement data 10 is within the tolerable range with respect to the image shape and the image position of the image master data 9, the two are determined to be a match and the engravings 8 in the surface 7a of the side plate 7 are determined to be suitable. If the result is that of being outside the tolerable range, the engravings 8 are determined to be unsuitable.

In the comparison processing of the present technology described above, two-dimensional data is compared. Accordingly, it can be determined whether or not the image shape and the image position of the image actual measurement data 10 is within a tolerable range with respect to the image shape and the image position of the image master data 9 in a reduced inspection time and with high precision. Additionally, inspection of small engravings 8 a few millimeters in size (for example, from 1 mm to 2 mm), that are difficult to determine the suitability of visually, is possible in a reduced inspection time and with high precision.

For example, in the image master data 9, the data of the engravings 8 (the engraving 8a for example), which is to be the extracted reference upon comparison processing, can be input into the data processing device 2 as extracted reference engraving data. Upon comparison processing of the image contours of the image master data 9 and the image actual measurement data 10, extracted reference engraving corresponding data (engraving 8a) in the image actual measurement data 10, which corresponds to the extracted reference engraving data (engraving 8a), is automatically extracted by the data processing device 2. Additionally, preliminary alignment of the images of the image master data 9 and the image actual measurement data 10 can be performed by aligning (aligning in the X direction) the images of the extracted reference engraving data (engraving 8a) and the extracted reference engraving corresponding data (engraving 8a). By performing this rough preliminary alignment automatically with the extracted reference engraving data as an indicator, operation man-hours can be greatly reduced. As the extracted reference engraving data, for example, an appropriate engraving 8 such as the largest of the engravings 8 can be employed.

After the preliminary alignment of the images of the image master data 9 and the image actual measurement data 10 described above, a detailed final alignment (alignment in the Y direction and small adjustments to the alignment in the X direction) of the images of the engravings 8a, 8b is performed.

The data of the engraving 8 in the side plate 7 determined to be suitable is stored in the data processing device 2 and can be used in the next determination of suitability. For example, upon the next determination of suitability, the acquired and generated image actual measurement data 10 of the engraving 8 in the side plate 7 can be compared to the previous image actual measurement data 10 stored in the data processing device 2 to keep track of changes over time. By doing so, an appropriate service life of the side plate 7 can be determined.

The invention claimed is:

1. A method, comprising:
   inspecting engravings in a tire mold to determine suitability of an engraving formed on a surface of an annular side plate, which is a component of the tire mold, wherein the engravings are inspected by:
      inputting into a data processing device two-dimensional image master data of the engraving formed on the surface of the annular side plate in a plan view pregenerated using a basic data set as a reference, the image master data having a radial component and a radial position of the engraving corrected on the basis of a locus length in a radial direction of the surface of the annular side plate, wherein the two-dimensional image master data represents only two dimensions of the engraving;
      acquiring three-dimensional data of the engraving by actual measurement of the annular side plate as manufactured;
      generating two-dimensional image actual measurement data, the image actual measurement data having a radial component and a radial position of the three-dimensional data corrected on the basis of a radial locus length of the surface of the annular side plate on which actual measurement was performed; and
      determining whether or not an image shape and an image position of the image actual measurement data is within a tolerable range with respect to an image shape and an image position of the image master data via comparison processing of image contours of the image master data and the image actual measurement data by the data processing device; wherein
   data of an engraving to be a reference in the image master data is input into the data processing device as reference engraving data, and upon the comparison processing of the image contours of the image master data and the image actual measurement data, reference engraving corresponding data in the image actual measurement data corresponding to the reference engraving data is automatically extracted by the data processing device, the method further comprising the steps of:
      performing preliminary alignment of images of the image master data and the image actual measurement data by alignment processing of images of the reference engraving data and the reference engraving corresponding data; and
      performing final alignment processing of the images of the image master data and the image actual measurement data after the preliminary alignment of the images of the image master data and the image actual measurement data.

2. A device for inspecting engravings in a tire mold capable of determining suitability of an engraving formed on a surface of an annular side plate, which is a component of the tire mold, the device comprising:
  a data processing device configured to receive two-dimensional image master data of the engraving formed on the surface of the annular side plate in a plan view using basic data set as a reference, wherein the two-dimensional image master data represents only two dimensions of the engraving, the image master data having a radial component and a radial position of the engraving corrected on the basis of a locus length in a radial direction of the surface of the annular side plate, wherein the data processing device is further configured to receive data of a reference engraving to be a reference in the image master data as reference engraving data; and
  a measuring unit configured to acquire three-dimensional data of the engraving by actual measurement of the annular side plate as manufacture; wherein
  two-dimensional image actual measurement data is generated by the data processing device, the image actual measurement data having a radial component and a radial position of the three-dimensional data corrected on the basis of a radial locus length of the surface of the annular side plate on which actual measurement was performed;
  whether or not an image shape and an image position of the image actual measurement data is within a tolerable range with respect to an image shape and an image position of the image master data is determined via comparison processing of image contours of the image master data and the image actual measurement data by the data processing device; and
  the data processing device is further configured to:
    automatically extract reference engraving corresponding data in the image actual measurement data corresponding to the reference engraving data;
    perform preliminary alignment of images of the image master data and the image actual measurement data by alignment processing of images of the reference engraving data and the reference engraving corresponding data; and
    performing final alignment processing of the images of the image master data and the image actual measurement data after the preliminary alignment of the images of the image master data and the image actual measurement data.

3. The device for inspecting engravings in a tire mold according to claim 2, wherein the measuring unit includes an irradiating device configured to irradiate the surface of the annular side plate with a laser, and a camera device configured to acquire the three-dimensional data by capturing an image of the engraving irradiated by the laser.

4. The device for inspecting engravings in a tire mold according to claim 3, further comprising a rotation mechanism configured to actuate rotational movement of the annular side plate and the camera device relative to one another about an annular center point of the annular side plate.

* * * * *